(12) United States Patent
Roubos et al.

(10) Patent No.: US 11,406,523 B2
(45) Date of Patent: Aug. 9, 2022

(54) ORTHOSIS

(71) Applicants: Theo Roubos, Elwood (AU); Harry Petridis, Elwood (AU)

(72) Inventors: Theo Roubos, Elwood (AU); Harry Petridis, Elwood (AU)

(*) Notice: Subject to any disclaimer, the term of this patent is extended or adjusted under 35 U.S.C. 154(b) by 78 days.

(21) Appl. No.: 16/630,012

(22) PCT Filed: Jul. 12, 2018

(86) PCT No.: PCT/AU2018/050718
§ 371 (c)(1),
(2) Date: Jan. 10, 2020

(87) PCT Pub. No.: WO2019/010534
PCT Pub. Date: Jan. 17, 2019

(65) Prior Publication Data
US 2021/0085507 A1 Mar. 25, 2021

(30) Foreign Application Priority Data

Jul. 12, 2017 (AU) .............................. 2017902736

(51) Int. Cl.
*A61F 5/02* (2006.01)
*A61F 5/058* (2006.01)
(Continued)

(52) U.S. Cl.
CPC .......... *A61F 5/05891* (2013.01); *A61F 5/022* (2013.01); *B29C 44/0407* (2013.01); *B29C 44/12* (2013.01)

(58) Field of Classification Search
CPC .. A61F 5/3707; A61F 5/05883; A61F 5/0102; A61F 5/01; A61F 13/12;
(Continued)

(56) References Cited

U.S. PATENT DOCUMENTS 5,722,102 A * 3/1998 Summers ............... A47C 7/425
297/452.29
6,071,257 A * 6/2000 Stojanovic ......... A41D 13/0512
128/845

(Continued)

FOREIGN PATENT DOCUMENTS

FR 2634119 A1 1/1990
WO 1995/020897 A1 8/1995

OTHER PUBLICATIONS

International Search Report, Australian Patent Office, dated Sep. 14, 2018.
(Continued)

*Primary Examiner* — Ophelia A Hawthorne
(74) *Attorney, Agent, or Firm* — Bay State IP, LLC

(57) ABSTRACT

An orthosis for treating a spine, the orthosis comprising a body having a base to support the orthosis on a surface and an upwardly facing surface having an undulating profile to align the spine of a user and support thoracic spinous processes of the spine, the upwardly facing surface including a longitudinal channel for receiving thoracic spinous processes of the user and a plurality of transverse channels that are arranged transversely to the longitudinal channel, wherein the undulating profile includes crests that are located on either side of the longitudinal channel.

16 Claims, 3 Drawing Sheets

(51) Int. Cl.
*B29C 44/04* (2006.01)
*B29C 44/12* (2006.01)

(58) Field of Classification Search
CPC .............. A61F 5/026; A61F 2007/0001; A61F
2007/0024; A61F 2013/00272; A61F
2013/00574; A61F 5/04; A61F 5/048;
A61F 5/05891; A61F 5/022; A61F 5/024;
A61F 5/028; A61F 5/37; A61H 1/008;
A61H 2201/1623; A61H 1/0292; A61H
2203/0456; A61H 1/0222; A61H
2205/081; A61H 2201/0192; A61H
2201/1664; A61H 2203/0468; A61H
23/006; A61H 7/002; B29C 44/0407;
B29C 44/12; A47C 7/40
See application file for complete search history.

(56) References Cited

U.S. PATENT DOCUMENTS

2015/0272808 A1   10/2015  Lee
2016/0136478 A1*  5/2016  Yu ...................... A63B 21/0004
                                                                       482/121
2017/0151117 A1*  6/2017  Chung ................. A61G 13/009

OTHER PUBLICATIONS

Written Opinion of the International Searching Authority, Australian Patent Office, dated Sep. 14, 2018.

* cited by examiner

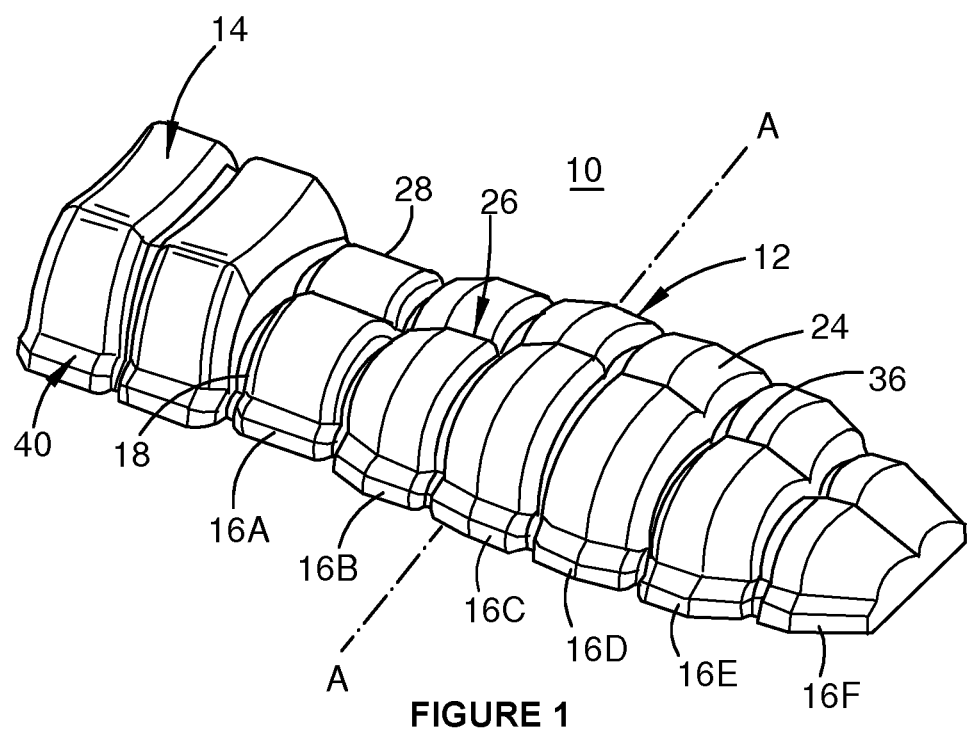
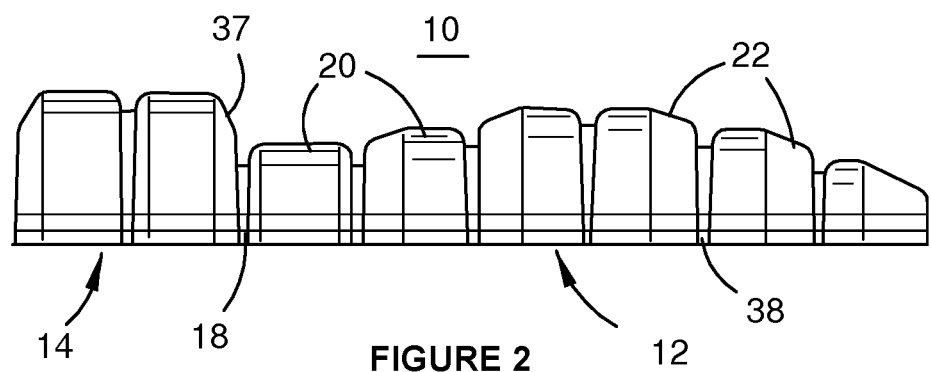

ORTHOSIS

CROSS REFERENCE TO RELATED APPLICATION

This application is for entry into the U.S. National Phase under § 371 for International Application No. PCT/AU2018/050718 having an international filing date of Jul. 12, 2018, and from which priority is claimed under all applicable sections of Title 35 of the United States Code including, but not limited to, Sections 120, 363, and 365(c), and which in turn claims priority under 35 USC 119 to Australian Patent Application No. 2017902736 filed on Jul. 12, 2017.

FIELD OF INVENTION

The present invention relates to a device for modifying the structural and/or functional characteristics of the neuromuscular and/or skeletal system of a user. Suitably, the present invention relates to a device for modifying the structural and/or functional characteristics of the spine of a user.

BACKGROUND OF THE INVENTION

An orthosis is an externally applied device used to modify the structural and/or functional characteristics of the neuromuscular and skeletal system.

A spinal orthosis uses a person's body weight to facilitate spinal alignment.

A conventional spinal orthosis is typically a cylindrical foam roller that includes a plurality of projections along the length of the roller.

During treatment, a user lies directly on the foam roller which is oriented transverse to the user's spine. The projections on the orthosis stimulate muscular trigger points and the person's body weight over the projections provides traction and extension to the spine.

The small surface area provided by conventional spinal orthoses may cause a number of problems.

In one example, the small surface area may increase the risk of the spine hyperextending and overstretching which can lead to micro trauma and injury.

In another example, the small surface area provides minimal stability for stretching the spine. As a result, the user may have to contract stabilizing spinal muscles to avoid rolling off the conventional spinal orthosis during treatment, which is undesirable. Lying across such a foam roller can also exert too much force directly on the spinous processes of the thoracic spine.

In another example, the small surface area of the foam roller requires the foam roller or the user to constantly adjust during treatment in order to treat the entire spine. As such, that there is a high risk of injury if the user is not provided with specific instructions and support when using the foam roller.

Accordingly, it may be desirable to provide an orthosis for treating a spine which can be used with minimal instructions and with a static application.

SUMMARY OF THE INVENTION

In one form, the present invention provides an orthosis for treating a spine, the orthosis comprising a body having a base to support the orthosis on a surface and an upwardly facing surface having an undulating profile to align the spine of a user and support thoracic spinous processes of the spine, the upwardly facing surface including a longitudinal channel for receiving thoracic spinous processes of the user and a plurality of transverse channels that are arranged transversely to the longitudinal channel, wherein the undulating profile includes crests that are located on either side of the longitudinal channel.

Ideally, the transverse channels intersect the longitudinal channel.

Crests may also form on at least one side of each transverse channel. Suitably, crests form on each side of the transverse channel.

The crests may be in the form of nodules located between the longitudinal channel and the transverse channels.

The plurality of projections may be spaced apart by the longitudinal channel and the transverse channels.

One advantage of the orthosis is that it can be used with minimal instruction and with a static application. It is not necessary to dynamically or actively manipulate the orthosis or adjust the position of the user during treatment. However, the user may adjust their arm position to facilitate treatment. For example, the user can have their arms at 90° abduction and at 180° abduction.

The orthosis may provide dynamic stretching of the spine using passive and/or active mobilisation techniques.

The base may include a flange to increase the stability of the orthosis when placed on the ground. In contrast, conventional spinal orthosis are cylindrical in shape and would roll when placed on the ground. This may adversely affect the treatment process if the user is not instructed on use of the conventional spinal orthosis properly.

The undulating profile may comprise between fourteen to four crests. Suitably, the undulating profile comprises six crests on either side of the longitudinal channel.

The body may comprise between four to fourteen nodules. Each nodule may comprise one or more crests. Suitably, the body comprises six nodules.

Suitably, a transverse channel is located between the six nodules.

The transverse channels between each crest may improve distribution of a user's weight.

The nodules may stimulate muscular trigger points, provide extension and/or traction to the thoracic spine.

The nodules may be shaped to accommodate the spinous processes of the thoracic spine. This reduces direct body weight on the spinous processes to reduce strain or injury.

The body may have a lateral cross-sectional profile that is "M" shaped, wherein crests on either side of the longitudinal channel form the arches of the "M" shape and the longitudinal channel forms the valley of the "M" shape.

A portion of the underside of the body may be hollow. This reduces the weight and material cost of the orthosis.

The underside of the body may include ribs to increase the structural integrity of the body by maintaining the form of the orthosis. Suitably, the ribs extend transversely to the length of the body. More suitably, the ribs extend from the transverse channels into the underside of the body.

Each transverse rib may have a thickness ranging from 10-30 mm. Suitably, each transverse rib has a thickness of about 25 mm.

The underside of the body may include a least two ribs. Suitably, the underside of the body includes four ribs.

The two arches/crests of the "M" shaped profile may further increase the stability and rigidity of the body.

The arches of the "M" shaped profile may provide lateral stability of the thoracic spine by supporting the transverse processes of the thoracic vertebrae.

In an embodiment, the body comprises six nodules, wherein each nodule has a generally "M" shaped profile. In other words, each nodule comprises two crests. The valley of each "M" shaped nodule may form part of the longitudinal channel.

The longitudinal channel may be discontiguous. Suitably, the longitudinal channel is formed by aligning the valleys of the "M" shaped nodules, which are intersected by the transverse channels.

Each crest may have a width ranging from 50-80 mm. Suitably, each crest has a width ranging from 60-70 mm. More suitably, each crest has a width of about 65 mm.

The transverse channels may allow independent movement of the nodules.

The transverse channels may have a width ranging from 2-10 mm. Suitably, the transverse channels have a width of about 5 mm.

The crests may reduce any one or more of strain, lateral deviation and rotation of the thoracic spinous processes.

The orthosis may support and elevate a substantial length of the spine of the user from the ground at any one time. In contrast, a conventional spinal orthosis, in the form of a foam roller, can only contact a small surface area of the spine at any one time. This may strain the spine and increase direct body weight on the spinous processes of the thoracic spine. Such a foam roller may also cause lateral deviation and rotation of the spinous processes.

The orthosis may provide simultaneous alignment of the spinous processes of the user's spine. In contrast, a conventional spinal orthosis, in the form of a foam roller, may only treat one section of the user's spine at any one time.

The body may be formed from a polymeric material, for example, polyethylene, polyethylene terephthalate, polypropylene, poly(ethylene-vinyl acetate) (pEVA), polystyrene, polyvinylchloride, acrylonitrile butadiene styrene (ABS), high impact polystyrene (HIPS) or high density polypropylene.

The body may be formed from a compressible foam. Suitably, the body may comprise a single piece of foam.

The body may be compressible to provide a soft surface for a user to lie on. The body may be formed from a foam. Suitably, the foam is closed cell foam rubber, for example, poly(ethylene-vinyl acetate) foam.

The compressible body may provide comfort to a user and minimise the likelihood of injury.

The body may include a rigid core to provide strength and rigidity. The core may be formed from a polymeric material, for example, polyethylene, polyethylene terephthalate, polypropylene, polystyrene or polyvinylchloride. Suitably, the core is formed from acrylonitrile butadiene styrene (ABS), polypropylene, high impact polystyrene (HIPS) or high density polypropylene.

The core may have of the same shape/profile as the body.

The core may have a thickness ranging from 1-10 mm, preferably 2-8 mm, even more preferably, 3-5 mm.

The body may include a compressible outer layer to provide a soft surface for a user to lie on. The compressible outer layer may be a foam layer. Suitably, the compressible outer layer is closed cell foam rubber, for example, poly(ethylene-vinyl acetate) foam. Other suitable materials for the compressible outer layer include polystyrene or polyurethane.

The compressible outer layer may have a thickness of 5-20 mm thick compressible layer. Preferably, the compressible outer layer has a thickness of 10-15 mm.

The compressible outer layer may provide comfort to a user and minimise the likelihood of injury.

Suitably, the body is a layered structure comprising a rigid core (endoshell) covered by a compressible outer layer (exoshell).

The orthosis may include a head rest. The head rest may provide support to the cervical spine. The head rest may reduce hyperextension of the cervical spine.

The head rest may be curved to accommodate the head of a user. Suitably, the head rest is concave.

The head rest may have a height ranging from 70-120 mm. Suitably, the head rest has a height ranging from 80-100 mm. More suitably, the head rest has a height of about 90 mm. Even more suitably, the head rest has a height of about 93 mm.

The head rest and the body may be integrally formed.

Alternatively, the head rest is formed separately from the body.

The body may be shaped to conform to the shape of the spine of a user. Suitably, the body has a generally convex profile which conforms to the profile of the spine of a user. In one example, the crests may have different heights along the longitudinal channel to form the generally convex profile.

In an embodiment where the crests are in the form of nodules, the nodules along the longitudinal channel have different heights to form the generally convex profile of the body.

Suitably, the crests/nodules increase in height from either end of the body to the middle of the body.

In another form, the present invention provides a method of forming an orthosis for treating a spine, the orthosis comprising a body having a base and an upwardly facing surface having an undulating profile, the upwardly facing surface including a longitudinal channel and a plurality of transverse channels that are arranged transversely to the longitudinal channel, wherein the undulating profile includes crests that are located on either side of the longitudinal channel, including the step of:

injecting a polymeric material into a mould having a shape corresponding to the shape of the body;

cooling the polymeric material; and demoulding the body.

The method of forming an orthosis for treating a spine may be automated.

The step of forming the body may include forming a head rest.

The step of forming the body may involve injecting a compressible polymer into the mould.

The method may involve heating the polymeric material before injection into the mould.

In another form, the present invention provides a method of forming an orthosis for treating a spine, the orthosis comprising a body having a base and an upwardly facing surface having an undulating profile, the upwardly facing surface including a longitudinal channel and a plurality of transverse channels that are arranged transversely to the longitudinal channel, wherein the undulating profile includes crests that are located on either side of the longitudinal channel, including the steps of:

forming a core; and coating a compressible layer to cover the core to form the body.

The method of forming an orthosis for treating a spine may involve overmolding.

The step of forming the core may involve forming a core having base and an upwardly facing surface including a longitudinal channel and a plurality of transverse channels intersecting the longitudinal channel, wherein crests form on either side of the longitudinal channel to form the undulating profile.

The step of forming the core may involve forming a core having base and an upwardly facing surface including a longitudinal channel and a plurality of transverse channels intersecting the longitudinal channel, wherein crests form on either side of the longitudinal channel and on at least one side of each transverse channel to form the undulating profile.

The step of forming the core may involve injecting a polymer into a mold having the desired profile to form a core having a thickness ranging from 1-10 mm, preferably 2-8 mm, even more preferably, 3-5 mm.

The step of forming the core may include forming a head rest.

The step of coating a compressible layer over the core may involve injecting a compressible polymer over the core.

The step of coating a compressible layer over the core may involve injecting a compressible polymer over the core to form a 5-20 mm thick compressible layer, preferably a 10-15 mm thick compressible layer.

The method of forming an orthosis for treating a spine may include connecting a head rest to the body.

BRIEF DESCRIPTION OF DRAWINGS

A preferred embodiment of the present invention is hereinafter described by way of example only, with reference to the accompanying drawings, wherein:

FIG. 1 is an isometric view of an orthosis according to one form of the present invention.
FIG. 2 is a side view of the orthosis of FIG. 1.

DETAILED DESCRIPTION

Figure 3:
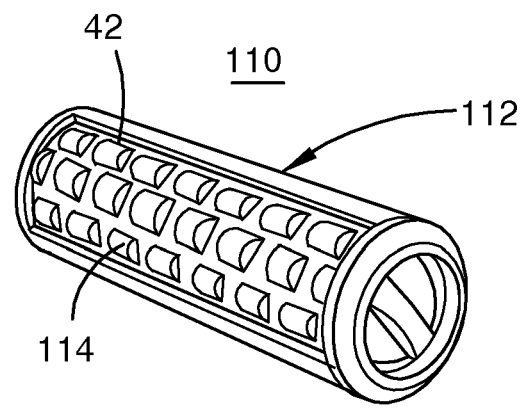
FIG. 3 is an isometric view of a conventional foam roller.

One aspect of an orthosis as defined by the invention is marked as 10 in FIG. 1.

The orthosis 10 comprising a body 12 having a flat base 38 and an upwardly facing surface having an undulating profile.

The orthosis 10 also includes a head rest 14. In FIG. 1, the body 12 and the head rest 14 are integrally formed.

The upwardly facing surface includes a longitudinal channel 36 and a plurality of transverse channels 18 which intersect the longitudinal channel 36. Crests form on either side of the longitudinal channel 36 and on at least one side of the transverse channels 18 to form the undulating profile.

In FIGS. 1 and 2, the crests are in the form of nodules 16A-F with a transverse channel 18 located between each nodule. Each transverse channel 18 has a width of about 5 mm. The head rest comprises two nodules 16G-H.

The body 12 has a generally convex profile which corresponds with the kyphotic profile of a user's thoracic spine. This provides support along a substantial portion of the user's spine during treatment and creates extension and traction through the spine. This can be done without the need for further manipulation of the orthosis 10 or movement from the user. However, the user may adjust their arm position to facilitate treatment. For example, the user can have their arms at 90° abduction and at 180° abduction.

Figure 5:
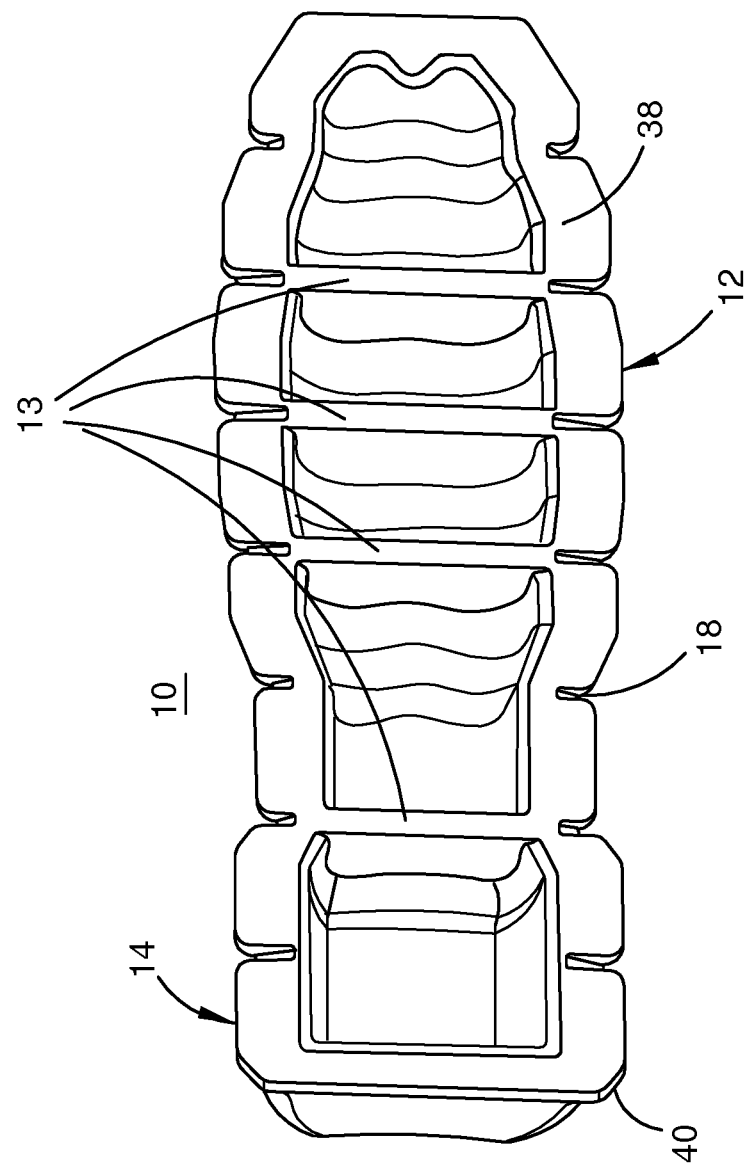
FIG. 5 is an underside view of the orthosis of FIG. 1.

The underside of the orthosis 10 is substantially hollow and has four 25 mm thick ribs 13 to maintain its shape and form (FIG. 5).

The nodules 16A-C and 16D-F have different heights such that the nodules increase in height from either ends of the body 12 (i.e. 16A or 16F) to the middle of the body 12 (i.e. 16C and 16D). This creates the generally convex profile of the body 12 (FIG. 2).

Each of the nodules 16A-F provides a flat longitudinal cross-sectional profile 20. Each of nodules 16B-F further includes a sloped longitudinal cross-sectional profile 22. More specifically, beginning at nodule 16A, the variation in profile of the body 12 follows a flat-sloped-flat profile until nodule 16C. From nodule 16D, the flat-sloped-flat profile is repeated until nodule 16F (FIG. 2). It is believed this profile variation enhances support of the user's thoracic spine.

Additionally, each of nodules 16A-F has a generally "M" shaped lateral cross-sectional profile 24 along the A-A axis, wherein a valley 26 is located between the two crests 28 of the "M" shape (FIG. 1). The width of each nodule 16A-H is about 65 mm.

Figure 4:
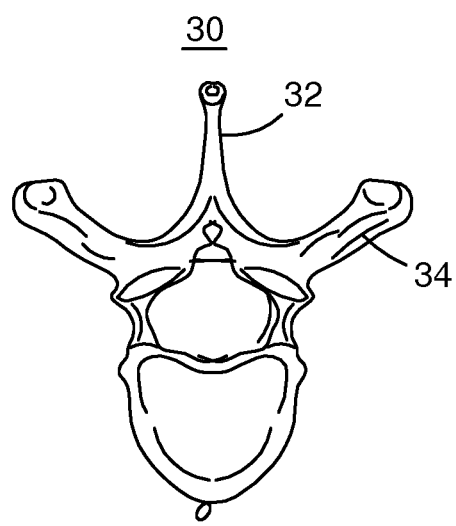
FIG. 4 is an illustration of a typical thoracic vertebra.

The "M" shape of each of nodules 16A-F supports the thoracic vertebrae 30 (FIG. 4) of the user's spine by having a profile which complements the profile formed by the spinous 32 and transverse processes 34 (FIG. 4).

The longitudinal channel 36 is formed by alignment of the valleys 26 of the "M" shaped nodules 16A-F, such that each valley 26 forms part of the longitudinal channel 36. Each of the six nodules 16A-F can accommodate two of a user's 12 thoracic vertebrae.

The longitudinal channel 36 aligns and supports the spine of a user. It is believed that the surface profile of each nodule 16A-F, particularly the crests of each nodule, enhances the support provided to a user's spine by supporting the transverse processes 34 and thus reducing the amount of weight exerted on the spinous processes 32.

The transverse channels improve distribution of the user's weight on the orthosis 10 and enable independent movement of the nodules 16A-H.

The head rest 14 is curved to accommodate the head of a user and includes a sloped edge 37. The head rest, provides cervical support and reduces hypertension of the cervical spine. The head rest 14 has a height of about 93 mm.

The flat base 38 includes a flange 40 to increase the stability and minimise movement of the orthosis 10 when placed on the ground. In contrast, a conventional spinal orthosis 110 (FIG. 3) is typically cylindrical in shape and would roll when placed on the ground.

The body 12 of the orthosis 10 comprises a single piece of pEVA foam.

The compressible body provides a soft surface for the user to lie on and to minimise injury.

The orthosis 10 is formed by injection moulding. This is done by heating pEVA foam to a temperature to reach a desired viscosity, injecting pEVA foam into a mould having the profile of the body, cooling the pEVA foam, and demoulding the body. The profile of the mould may include a head rest as illustrated in FIGS. 1 and 2.

A comparison would now be made between treatment using a conventional spinal orthosis and an orthosis according to the present invention.

During conventional treatment, a conventional spinal orthosis 110 (FIG. 3) comprising a foam roller 112 having a plurality of projections 114 along the length of the roller is used.

During this treatment, a user lies on the foam roller 112 (FIG. 3) such that the foam roller is positioned transverse to the user's spine. Because the foam roller 112 can only contact a small surface area of the user's spine at any one time, either the foam roller 112 to be manipulated or the user has to move during treatment to treat all parts of the user's spine. Disadvantageously, the spine of the user at any one time during treatment would be strained into an unnatural shape because the foam roller 112 is unable to support the entire length of the spine at any one time.

In contrast, during treatment using the orthosis 10, a user lies on the orthosis 10 such that their thoracic spine rests on the six nodules 16A-F, and their head rests on the head rest 14. In this position, most if not all of the user's spine is elevated and supported by the orthosis 10. This provides simultaneous alignment of the thoracic vertebrae of the user's spine.

The thoracic spinous processes 32 of the user rests on the valleys 26 of the nodules 16A-F, and the crests 28 of the nodules 16A-F support the transverse processes 34 of the thoracic vertebrae. This provides lateral stability and reduces lateral deviation and rotation of the thoracic spinous processes 32. This also reduces direct body weight on the thoracic spinous processes and minimises strain or injury to the user.

No further manipulation of the orthosis is required during treatment as the nodules 16A-F stimulate muscular trigger points, and provide extension and traction to the thoracic spine.

The invention claimed is:

1. An orthosis for treating a spine, the orthosis comprising:
a body having a base to support the orthosis on a surface and an upwardly facing surface having an undulating profile to align the spine of a user and support thoracic spinous processes of the spine, the upwardly facing surface including a longitudinal channel for receiving thoracic spinous processes of the user and a plurality of transverse channels that are arranged transversely to the longitudinal channel, wherein the undulating profile includes crests that are located on either side of the longitudinal channel; and
wherein the crests have different heights along the longitudinal channel to form a generally convex profile.

2. The orthosis according to claim 1, wherein a portion of an underside of the body is hollow.

3. The orthosis according to claim 2, wherein the underside of the body includes ribs to increase the structural integrity of the body.

4. The orthosis according to claim 3, wherein the ribs extend transversely to a length of the body.

5. The orthosis according to claim 3, wherein the ribs extend from the transverse channels into the underside of the body.

6. The orthosis according to claim 1, wherein the crests are in the form of nodules are located between the longitudinal channel and the transverse channels.

7. The orthosis according to claim 6, wherein the nodules are shaped to accommodate the spinous processes of the thoracic spine of the user.

8. The orthosis according to claim 1, wherein the orthosis includes a head rest.

9. The orthosis according to claim 8, wherein the head rest is concave.

10. The orthosis according to claim 1, wherein the transverse channels intersect the longitudinal channel.

11. The orthosis according to claim 1, wherein crests are formed on at least one side of each transverse channel.

12. The orthosis according to claim 1, wherein the crests increase in height from either end of the body to the middle of the body.

13. The orthosis according to claim 1, wherein the body has a lateral cross-sectional profile that is "M" shaped, wherein crests on either side of the longitudinal channel form an arches of the "M" shape and the longitudinal channel forms a valley of the "M" shape.

14. The orthosis according to claim 1, wherein the longitudinal channel is discontiguous.

15. The orthosis according to claim 1, wherein the body is formed from a compressible foam.

16. The orthosis according to claim 1, wherein the base includes a flange to increase the stability of the orthosis when placed on a ground.

* * * * *